US010674930B2

(12) United States Patent
Sun et al.

(10) Patent No.: US 10,674,930 B2
(45) Date of Patent: Jun. 9, 2020

(54) SINGLE-UNIT LEADLESS EEG SENSOR

(71) Applicant: University of Pittsburgh-Of the Commonwealth System of Higher Education, Pittsburgh, PA (US)

(72) Inventors: Mingui Sun, Pittsburgh, PA (US); Bo Luan, Pittsburgh, PA (US); Parthasarathy Deenadayalan Thirumala, Glenshaw, PA (US); Wenyan Jia, Wexford, PA (US); Di Gao, Sewickley, PA (US); Jeffrey Balzer, Wexford, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 827 days.

(21) Appl. No.: 15/282,828

(22) Filed: Sep. 30, 2016

(65) Prior Publication Data
US 2017/0095176 A1 Apr. 6, 2017

Related U.S. Application Data

(60) Provisional application No. 62/236,013, filed on Oct. 1, 2015.

(51) Int. Cl.
*A61B 5/0478* (2006.01)
*A61B 5/00* (2006.01)

(52) U.S. Cl.
CPC .......... *A61B 5/0478* (2013.01); *A61B 5/0006* (2013.01); *A61B 5/6839* (2013.01); *A61B 5/7225* (2013.01); *A61B 2562/125* (2013.01)

(58) Field of Classification Search
CPC ... A61B 5/0476; A61B 5/0478; A61B 5/0402; A61B 5/0408; A61B 5/04085; A61B 5/7214; A61B 5/6814; A61B 5/6839
See application file for complete search history.

(56) References Cited

U.S. PATENT DOCUMENTS

| 6,385,473 | B1 * | 5/2002 | Haines | A61B 5/0006 600/382 |
| 8,112,139 | B2 | 2/2012 | Sun et al. | |
| 2008/0262335 | A1 * | 10/2008 | Sun | A61B 5/0478 600/372 |
| 2010/0042012 | A1 * | 2/2010 | Alhussiny | A61B 5/04085 600/546 |

(Continued)

OTHER PUBLICATIONS

Agarwal et al., "Portable cost-effective EEG data acquisition system," *J. Med Eng. Technol.*, 35:185-190 (2011).

(Continued)

*Primary Examiner* — Eun Hwa Kim
(74) *Attorney, Agent, or Firm* — Klarquist Sparkman, LLP

(57) ABSTRACT

Single-unit EEG sensors contain multiple closely spaced dry electrodes that can hook onto skin and associated electronic circuitry such as amplifiers, A/D convertors, wireless transmitters, and a power source such as a battery. The electrodes can be separated by about 20 mm or less, and the associated circuitry can be situated within a volume defined by the multiple electrodes. The single-unit sensors hook onto the skin using a tooth surface so that a rotation of the sensor secures and electrically connects the sensor to the skin.

23 Claims, 13 Drawing Sheets

(56) References Cited

U.S. PATENT DOCUMENTS

2011/0251469 A1* 10/2011 Varadan ................ A61B 5/113
600/301
2015/0126845 A1   5/2015 Jia et al.

OTHER PUBLICATIONS

Arnin et al., "Wireless-based portable EEG-EOG monitoring for real time drowsiness detection," *Conf. Proc. IEEE Eng. Med. Biol. Soc.*, 2013:4977-4980 (2013).

Badcock et al., "Validation of the Emotiv EPOC® EEG gaming system for measuring research quality auditory ERPs," *PeerJ*, 1:1-17 (2013).

Bashivan et al., "Mental State Recognition via Wearable EEG," *Proceedings of 5th NIPS workshop on Machine Learning and Interpretation in Neuroimaging*, available at: arXiv:1602.00985v2, 10 pages (submitted Feb. 2, 2016; last revised Jun. 5, 2016).

Besio et al., "Development of a tri-polar concentric ring electrode for acquiring accurate Laplacian body surface potentials," *Ann. Biomed. Eng.*, 34:426-435 (2006).

Besio et al., "Tri-polar concentric ring electrode development for Laplacian electroencephalography," *IEEE Trans. Biomed. Eng.*, 53:926-933 (2006).

De Lissa et al., "Measuring the face-sensitive N170 with a gaming EEG system: A validation study," *J. Neurosci. Methods*, 253:47-54 (2015).

"Disposable PressOn EEG Electrodes," Rhythmlink International, LLC, available at: http://rhythmlink.com, 1 page.

"Emotiv EPOC and EPOC+ Quick Start Guide," Emotiv, available at: https://www.emotiv.com, 1 page (Dec. 11, 2015).

Kolls et al., "Electroencephalography leads placed by nontechnologists using a template system produce signals equal in quality to technologist-applied, collodion disk leads," *J. Clin. Neurophysiol*, 29:42-49 (2012).

Krigolson et al., "Choosing MUSE: Validation of a Low-Cost, Portable EEG System for ERP Research," *Frontiers in Neuroscience*, 11:1-10 (Mar. 2017).

Luan et al., "A Feasibility Study on a Single-Unit Wireless EEG Sensor," *International Conference on Signal Processing*, IEEE, pp. 2282-2285 (Oct. 2014).

Mirsattari et al., "MR imaging-compatible electroencephalography electrode system for an epilepsy monitoring unit," AJNR AM. J. Neuroradiol., 29:1649-1651 (2008).

Scherg et al., "Two bilateral sources of the late AEP as identified by a spatio-temporal dipole model," *Electroencephalogr. Clin. Neurophysiol.*, 62:32-44 (1985).

"The brain sensing headband," Muse, available at: http://choosemuse.com, 3 pages, retrieved Sep. 12, 2017.

"Wearable and wireless EEG system," Mindo, available at: http://mindo.com.tw/, 7 pages, retrieved Sep. 12, 2017.

* cited by examiner

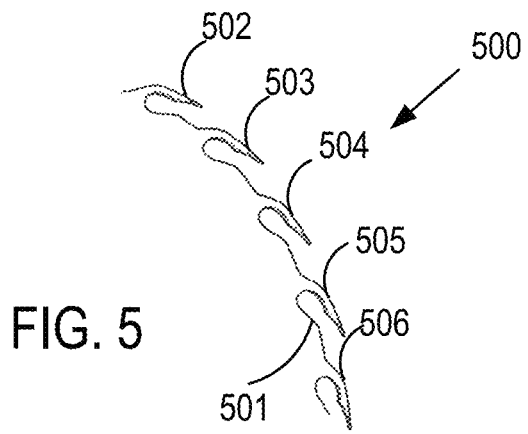
FIG. 5
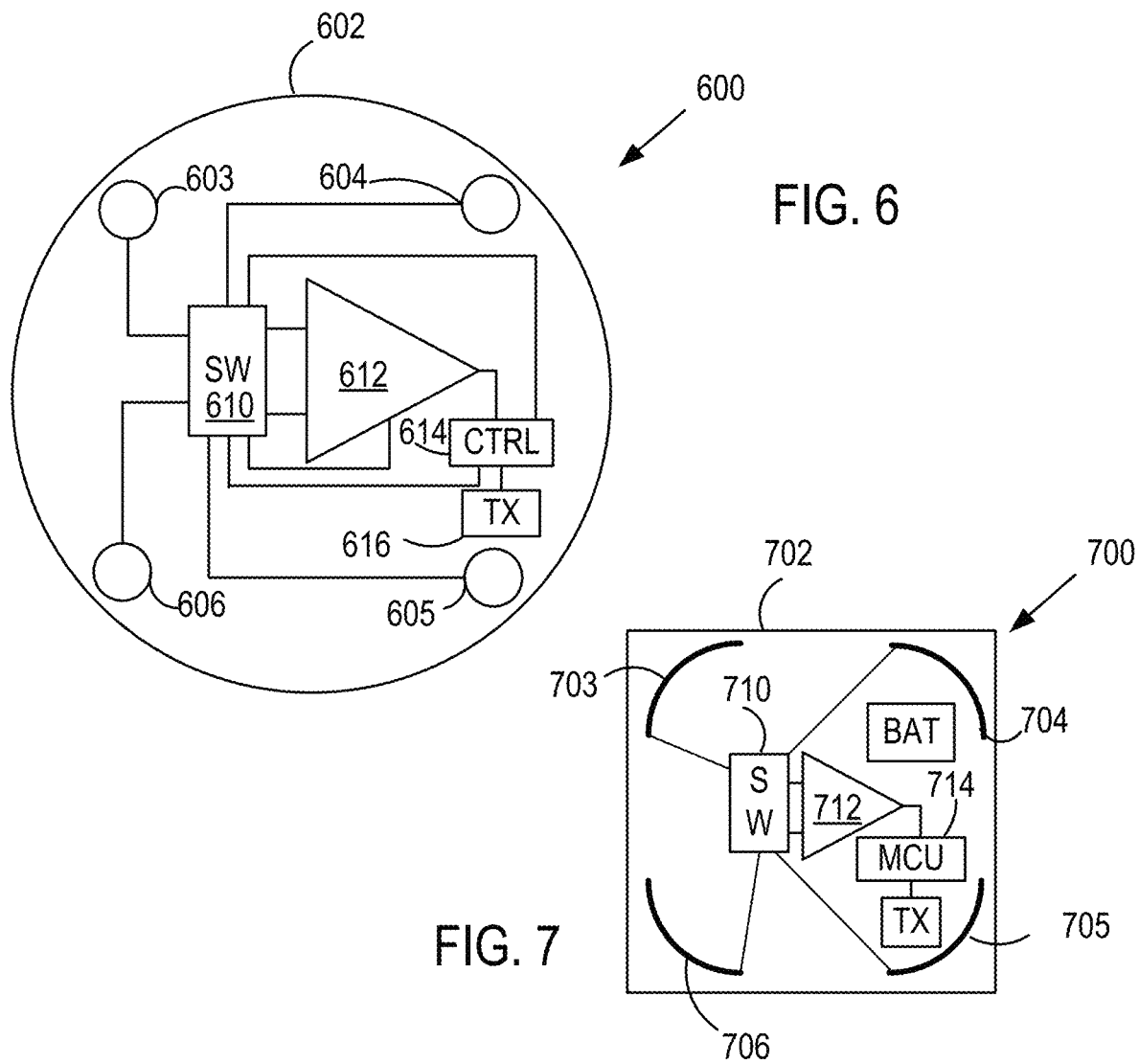
FIG. 6
FIG. 7

FIG. 18
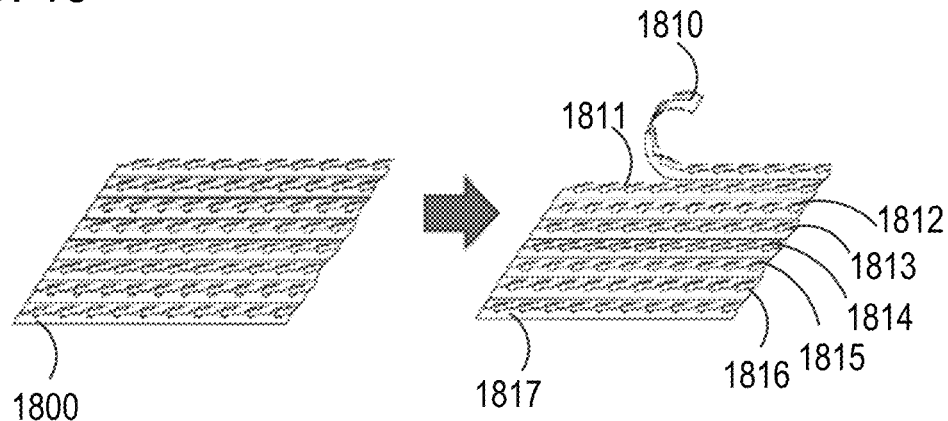
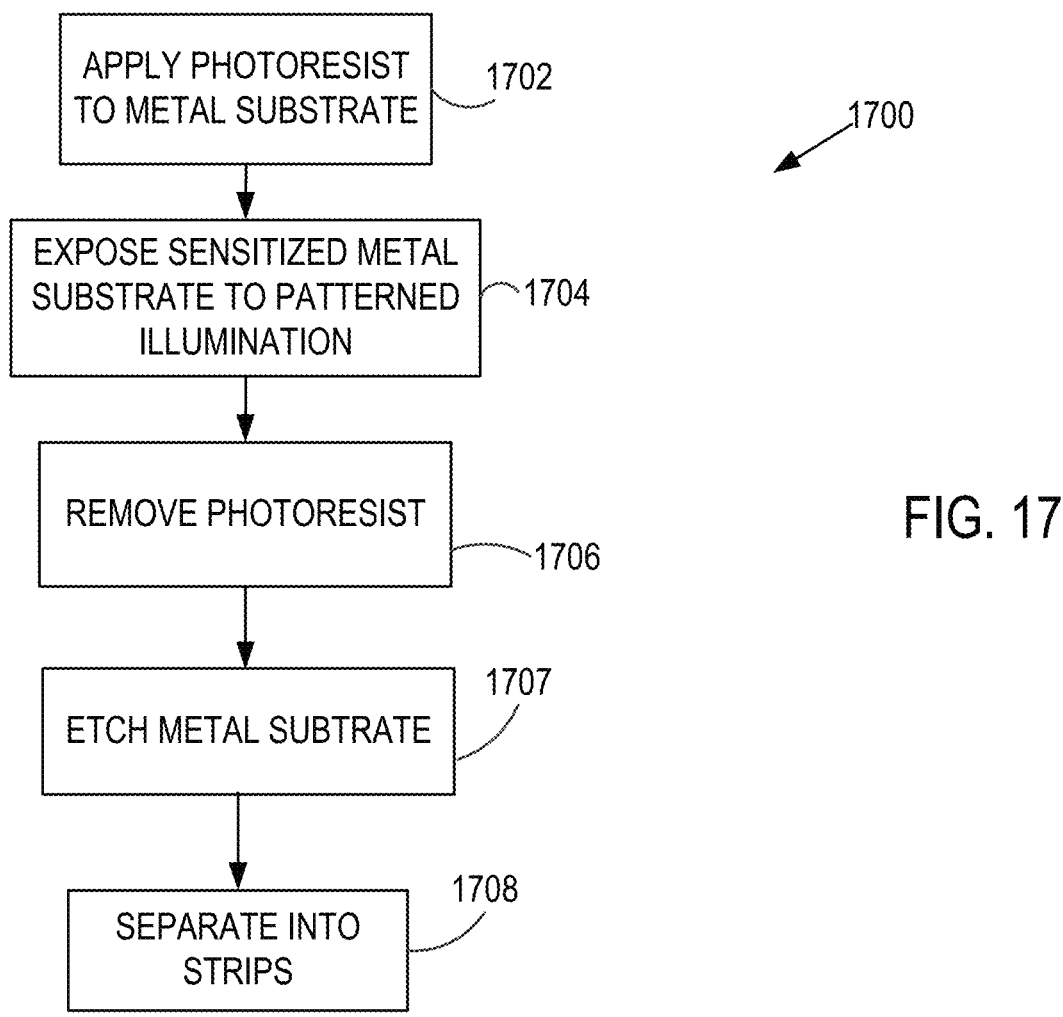
FIG. 17

SINGLE-UNIT LEADLESS EEG SENSOR

CROSS REFERENCE TO RELATED APPLICATION

This application claims the benefit of U.S. Provisional Application No. 62/236,013, filed Oct. 1, 2015, which is incorporated herein by reference in its entirety.

ACKNOWLEDGMENT OF GOVERNMENT SUPPORT

This invention was made with government support under Grant Nos. EB013174, and NS036888 awarded by the National Institutes of Health. The government has certain rights in the invention.

FIELD

The disclosure pertains to EEG measurement.

BACKGROUND

In clinical practice, rapid diagnosis of acute neurological diseases from electroencephalographic (EEG) observations is highly important. But the current method of affixing EEG electrodes to the scalp is tedious, taking several minutes for each electrode. In addition, to acquire a single channel of EEG, at least three electrodes must be wired (e.g., using electrode leads) to an amplifier. Wires tangling can cause signal distortion and it make it inconvenient to acquire EEG in emergency, mobile, and certain applications, such as in critical, ambulatory care or sleep studies. Although there are portable EEG devices available, these devices still require installation of multiple distinct electrodes on the scalp and wire connections to individual electrodes which consume precious time in critical care, and often cause wire tangling, signal interruption, and friction noise.

SUMMARY

The disclosed approaches can provide small, self-contained sensors to record EEG and wirelessly transmit data to one or more of a mobile device at the site of care and/or a remotely located medical service center.

EEG sensors comprise an electrode assembly that includes at least three EEG electrodes that are secured with respect to each other. An amplifier is coupled to the at least three EEG electrodes, such that first and second electrodes are coupled to respective differential amplifier inputs and a third electrode is coupled to the differential amplifier as a reference so as to produce an output signal associated with the at least three electrodes. A plurality of hooks is fixed with respect to the housing and is operable to secure the at least three EEG electrodes to a surface of a subject. In some examples, the sensors include an analog-to-digital convertor (ADC) coupled to an output of the differential amplifier so as to produce a digital signal corresponding to the differential amplifier output signal. A transmitter is coupled to the ADC so as to produce a transmitted signal associated with the digital signal corresponding to the differential amplifier output. A battery, for example, a polymer lithium-ion battery, serves as the power supply for the EEG sensor. Sensor electrodes can be provided on a disposable disk such as a plastic disk that retain the battery and can also include clips for battery connections and connection to amplifiers and other EEG circuit components.

In representative examples, the at least three electrodes have distal surfaces situated to engage a subject's scalp surface, and the electrode hooks are situated on the distal surfaces. In some examples, the electrode hooks extend at least partially laterally from the distal surfaces or at least partially axial from the distal surfaces. In typical examples, the perimeter of the housing is circular, and four electrodes are utilized in which two opposite electrodes are connected as the reference input of a differential amplifier, and the remaining two electrodes are connected to the differential inputs of the same amplifier. These four electrodes correspond to sections of a cylindrical shell and are situated adjacent the perimeter of the housing.

In further examples, the EEG sensors comprise a switch, in the form of either an electronic or a mechanical switch, coupled to the at least three electrodes so as to select the first and second electrodes to be coupled to the differential amplifier inputs and the third electrodes to be coupled as the reference. In still additional examples, the EEG sensor has four electrodes. The switch selects between two configurations in which two opposite electrodes are connected as the reference, as shown in FIG. 10, and a switch is coupled to four electrodes so as to select one opposite pair of electrodes to be coupled to the differential amplifier inputs and the remaining opposite pair of electrodes to be coupled as the reference. In representative embodiments, the wireless transmitter is a radio-frequency transmitter and the diameter of the EEG sensor is between 1.5 cm and 2 cm.

Electrode assemblies comprise an electrode substrate and at least three electrodes defined as conductive sections of a common cylinder and secured to an insulated electrode substrate. Each of the conductive sections extends along an axis of the common cylinder, and each of the at least three electrodes has a toothed distal surface for attachment to a skin surface. In representative examples, the electrode substrate is a cylindrical substrate and the at least three electrodes are secured to an internal or external surface of the cylindrical substrate so that each of the conductive sections defining the at least three electrodes extends along an axis of the cylindrical substrate. Typically, the cylindrical substrate is a hollow cylindrical substrate. In some examples, the tooth at edge of the electrodes includes a plurality of teeth, each of the plurality of teeth having a plurality of gold-coated tooth surfaces. In another embodiment, gold-coated, densely grown nanowires are extended perpendicularly to the surface of the electrode teeth to improve electrode contact with the skin. Typically, the teeth, with or without nanowires, have a tooth depth of less than 0.5 mm.

Methods comprise securing an electrode assembly that includes a plurality of electrodes fixed with respect to each other to a skin surface so as to electrically connect each of the plurality of electrodes to the skin surface. An electrical signal associated with at least three of the plurality of electrodes is processed (typically band-pass filtered) for transmission, and the processed signal is transmitted. In some examples, the electrode assembly is secured to the skin surface by a slight clockwise (or counter-clockwise) rotation so that a toothed surface engages and penetrates the very top layer skin surface (stratum corneum), and the electrical signal is transmitted as a radio-frequency signal.

The foregoing and other features, and advantages of the disclosure will become more apparent from the following detailed description, which proceeds with reference to the accompanying figures.

BRIEF DESCRIPTION OF THE DRAWINGS

FIG. 5 illustrates a portion of an EEG electrode having microscopic hooks so as to provide electrical and mechanical coupling to a subject's skin surface.

FIGS. 6-7 are schematic plan views of representative EEG sensors having disk-shaped arc segments, respectively, that serve as EEG electrodes.

FIGS. 17-18 illustrate a representative method of manufacturing sensor electrodes.

DETAILED DESCRIPTION

Figure 1:
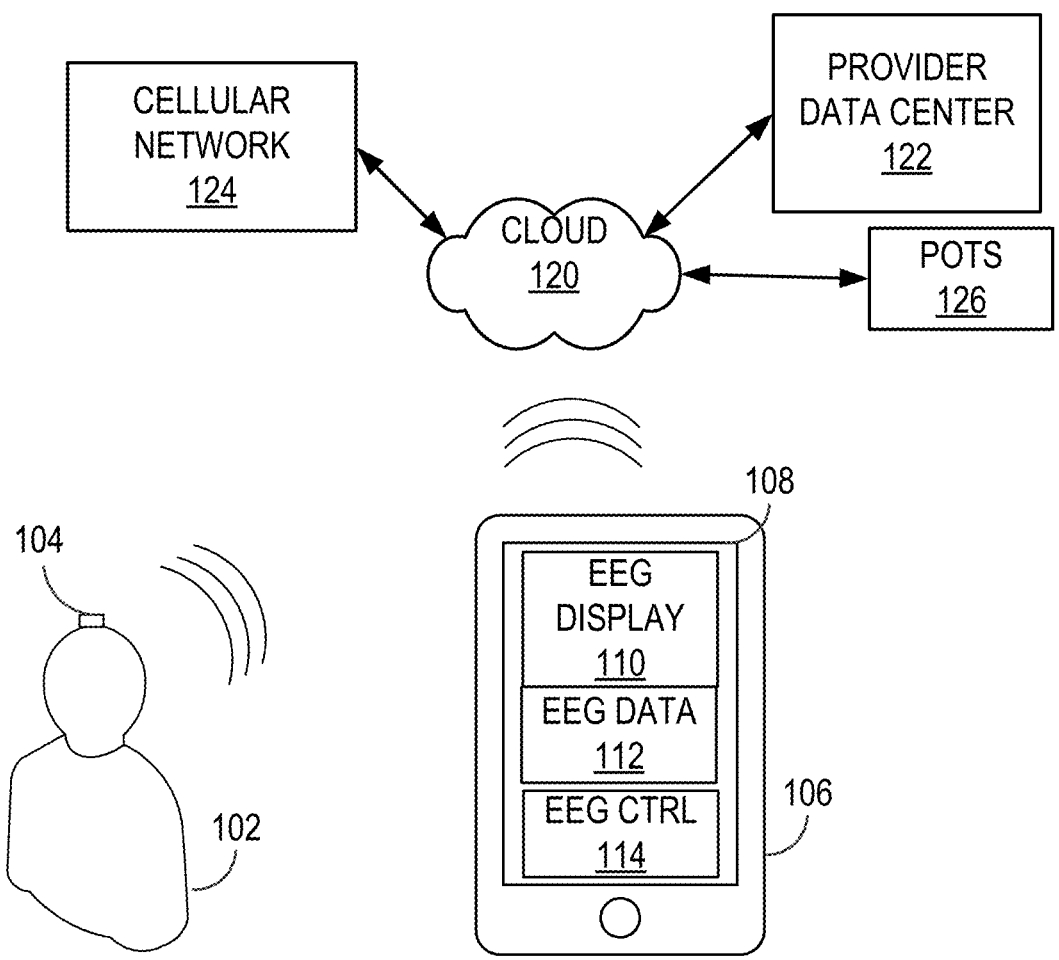
FIG. 1 illustrates communication of EEG data from an EEG sensor to a mobile computing device and a wide-area network (cloud) that is coupled to additional communication channels and to medical provider networks and databases.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items unless otherwise noted.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

Examples are described in some cases with reference to directions indicated as "above," "below," "upper," "lower," and the like. These terms are used for convenient description, but do not imply any particular spatial orientation. EEG electrode separations as disclosed herein are typically less than about 30 mm, 25 mm, 20 mm, 15 mm, 10 mm, or 5 mm as measured center-to-center, but other separations can be used.

In the disclosed examples, two, three, or more electrodes are fixed with respect to each other for convenient attachment to subject surface. As used herein, a substrate or housing refers to a supporting structure to which such electrodes are fixed. In typical examples, such a supporting structure also defines a volume in which associated sensor electronics can be situated. Substrates or housings need not define such volumes, and electronic circuitry can be secured to a substrate or housing, or otherwise fixed with respect to a substrate or housing. However, such electronic circuitry can be remotely located, although such an arrangement is generally inconvenient and less desirable.

EEG waveforms and data are typically transmitted from a sensor without a wired connection. As used herein, radio-frequency transmission includes transmission at frequencies between about 10 kHz and 20 GHz, typically at frequencies associated with one or more communication standards such a BLUETOOTH, WIFI, of Near Field Communication (NFC) standard.

In typical examples, single-unit, ultra-portable EEG sensors can be provided that are smaller than about 10 mm in height by 19 mm in diameter, permitting rapid, convenient acquisition of critical point-of-care information about brain electrical activity. In some examples, a cylindrical EEG sensor is twisted and hooked onto a subject's skin surface without the need for skin preparation and electrolyte. Electronic components such as amplifiers, analog-to-digital converters (ADCs), filters, microcontrollers, wireless transmitters, receivers, antennas, and other components are placed within the sensor. The EEG sensor transmits EEG data to a data port such as a mobile computing device, a tablet computer, a lap top computer, a desktop computer, or other fixed or mobile devices. The transmitted EEG data can be distributed via the cloud to one or more additional destinations as may be desired. From the data port, the EEG waveforms can be observed or further transmitted to a remotely located server or a cloud platform.

EEG electrode assemblies typically include three or more electrodes that are fixed with respect to each other. The electrodes can be secured to a substrate, a housing, or other support structure or secured to each other. The electrodes are separated by one or more insulators or are otherwise electrically selected, and electrodes for a particular measurement can be selected using a switch such as a mechanical switch or an analog switch. In some examples, four electrodes are provided and one opposing pair of electrodes is electrically coupled to serve as a reference and a second opposing pair of electrodes is coupled for use in measurement. For convenience, surfaces of electrodes configured for attachment to a subject are referred to as "distal surfaces."

With reference to FIG. 1, a representative diagnostic system for acquiring EEG waveforms from a subject 102 includes a head-mounted EEG sensor 104 that typically includes at least three electrodes, amplifiers, buffers, and a transmitter and other circuitry to process EEG signals for wireless communication. A mobile device 106 is situated to receive the communicated EEG waveforms based on processor-executable instructions stored in the mobile device 106. A mobile device display 108 is generally arranged to provide display regions 110, 112, 114 for display of EEG waveforms, related EEG waveform data or measurement results, and EEG data acquisition and communication controls such as acquisition duration, electrode selection, waveform and data storage, communication destination, and method of communication (e.g., email, text message, posting to cloud-based server). The mobile device 106 wirelessly communicates EEG waveform and other data via a wide area network 120 ("cloud") to a provider data center 122. In some cases, EEG waveforms and other data are relayed to a cellular network 124 or a conventional telephone network (POTS) 126. EEG data can be encrypted prior to transmission for privacy, and transmission can be authorized only to validated addresses such as email addresses, IP addresses, or other destination identifiers.

In other examples, the EEG sensor 104 can be coupled to a mobile device or other data acquisition and control system using a wired connection, and the mobile device or data acquisition and control system can communicate to the cloud 120 using a wired connection such as an Ethernet connection. Wireless communication can be based on optical or radio-frequency communications, and suitable optical emitters (e.g., LEDs), optical detectors, and associated emitter drivers, detector amplifiers can be provided. Typically, radio-frequency or other wireless electrical communication is provided as convenient using communication systems such described by BLUETOOTH, NFC, or ZIGBEE wireless communication standards. The EEG sensor 104 typically communicates digitized EEG waveforms, but transmission of analog EEG waveforms is also possible, albeit generally less convenient. While FIG. 1 indicates communications from the EEG sensor 104, the mobile device 106 can also communicate data acquisition instructions, communication channel information, or other data or instructions to the EEG sensor 104.

Figure 2:
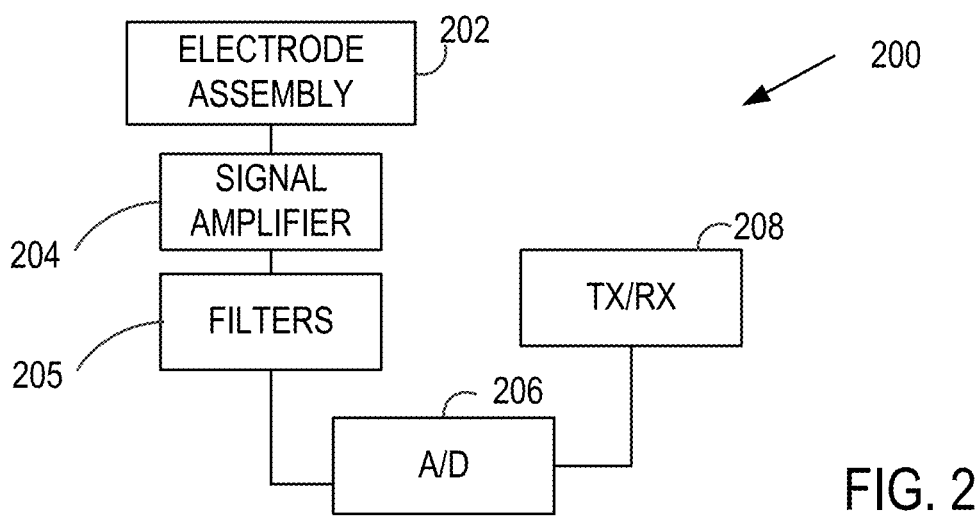
FIG. 2 is a schematic diagram of a representative EEG sensor.

Referring to FIG. 2, a representative EEG sensor 200 includes an electrode assembly 202 (typically at least three electrodes) that is coupled to a signal amplifier 204. The signal amplifier can filter and amplify EEG signals from the electrode assembly 202 and direct the processed signals to an analog-to-digital convertor 206 that produces digital representations of EEG waveforms. Typically, one or more filters 205 process the signals prior to the analog-to-digital convertor 206. The digital representations are coupled to a transmitter (TX) or transmitter/receiver 208 for communication to a mobile device or other destination. The electrode assembly 202 generally includes three or more electrodes that are fixed with respect to each other so as to be easily secured to a subject. In some cases, the electrodes are situated at, on, or proximate a perimeter surface of a housing or substrate to which the signal amplifier 204, A/D 206, and transmitter 208 are secured to provide a suitable large (or maximum) electrode spacing given an overall size of the EEG sensor 200.

Figure 3:
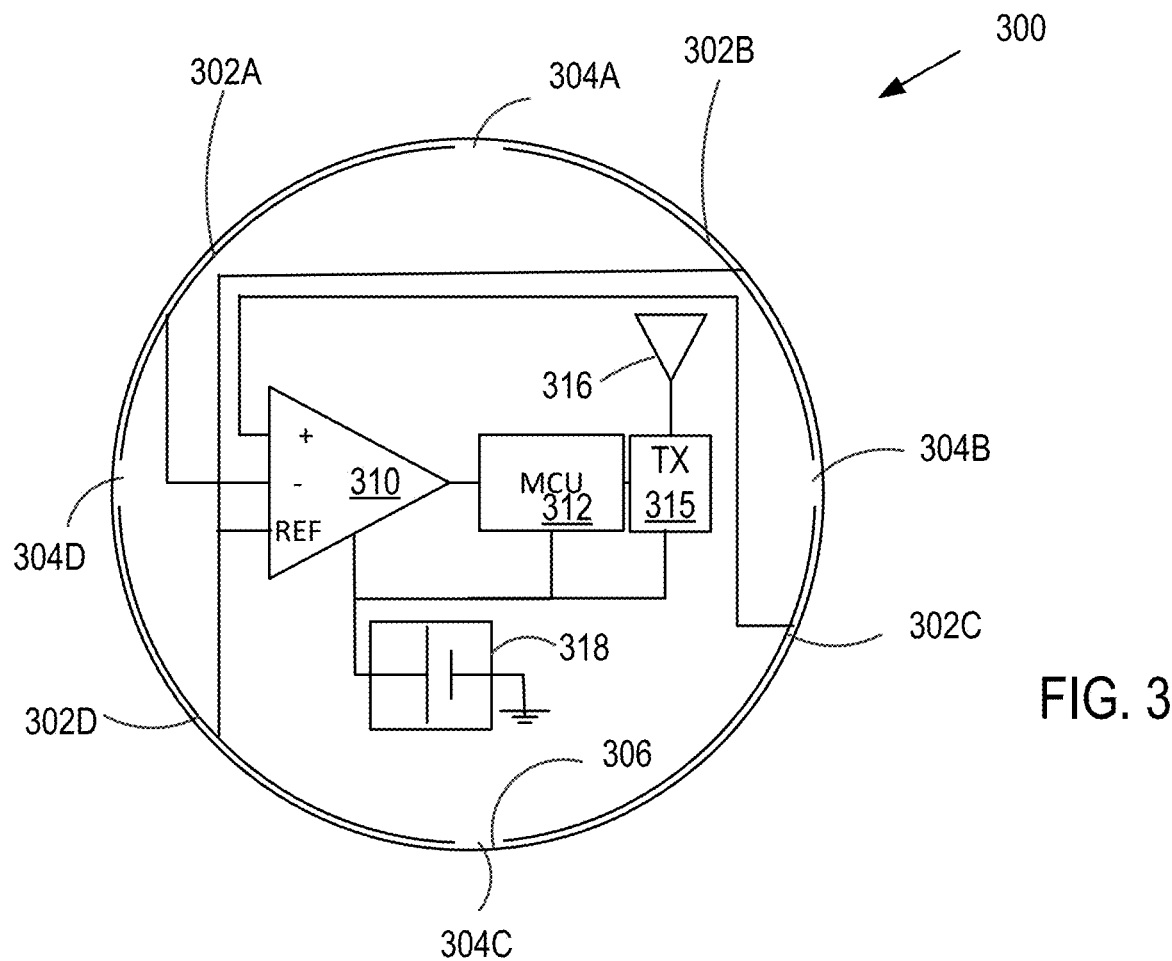
FIG. 3 is a schematic plan view of a representative EEG sensor having conductive arc segments that serve as EEG electrodes.

With reference to FIG. 3, a representative EEG sensor 300 includes electrodes 302A-302D that are secured to an interior surface of a housing 306. The electrodes 302A-302D are electrically separated with gaps 304A-304D. The electrodes 302A-302D can be formed of a wire mesh, as a conductive coating on the housing 306, or as discrete conductors, and can be provided as disposable electrodes. The electrodes 302A-302D are shown in FIG. 3 as extending along a substantial portion of an interior surface of a housing 306 having a circular cross-section, but the shape and extent of the electrodes can be selected as convenient, and the housing 306 can have square, rectangular, polygonal, arcuate or other cross-sections. By placing electrodes at a housing surface, electrode spacing can be increased to substantially a housing dimension. The electrodes 302A-302D can also be secured to or defined on a housing exterior surface.

A differential amplifier 310 has differential inputs coupled to electrodes 302A, 302C and a reference input coupled to electrodes 302B, 302D. An output of the differential amplifier 310 is coupled to a microcontroller (MCU) 312 for A/D conversion and other processing. The digital output is coupled to transmitter 315 and an antenna 316 for communication. Power is provided to the differential amplifier 310, the MCU 312, and the transmitter 315 with a battery 318.

Figure 4:
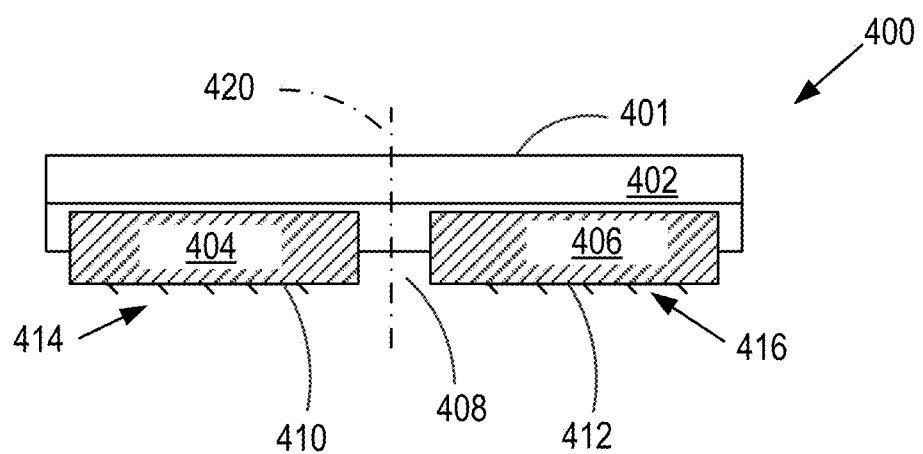
FIG. 4 is a schematic side view of a representative EEG sensor having conductive arc segments that serve as EEG electrodes.

FIG. 4 is side view of an EEG sensor 400 such as that of FIG. 3. The EEG sensor 400 includes a housing 401 that defines a battery compartment 402 and associated electronics (not shown in FIG. 4) and electrodes 404, 406 that are situated at an exterior surface of the EEG sensor 400. The electrodes 404, 406 are typically disposable and are electrically separated by a gap 408, and each of the electrodes 404, 406 includes a respective plurality 414, 416 of fasteners such as teeth, hooks, barbs, pins, clips, or others on respective distal surfaces 410, 412. As used herein, a distal electrode surface is an electrode surface that faces a subject surface (such as a patient's hair or skin) as situated to acquire EEG signals. As shown in FIG. 4, the fasteners 414, 416 extend axially beyond the distal surfaces 410, 412 (i.e., along an axis 420) but can extend laterally outwardly or inwardly (i.e., in directions perpendicular to the axis 420) as well. The fasteners 414, 416 are generally selected to provide mechanical and electrical coupling to a subject.

With reference to FIG. 5, a lateral exterior surface 501 of an electrode 500 includes hooks 502-506 that can be used to secure the electrode 500 to a subject. In the top down view of FIG. 5, a clockwise rotation causes the hooks 502-506 to engage so that the electrode 500 (and the EEG sensor) is mechanically fixed and electrically coupled to the subject.

Electrode gels are not needed, and electrodes can be placed with a simple rotation. EEG electrodes can also be provided on lateral or distal surfaces with barbs, needle-like, dentate or other protrusions, series of stiff wires or other protrusions that are aligned at an angle with respect to the distal surface of an electrode. Needles, wires, or other protrusions can also extend substantially perpendicularly to distal electrode surfaces. With such protrusions, electrical contact is made without necessarily providing sufficient mechanical attachment, and tapes, clips, bands, combs, or other structures can be used to secure the electrodes.

Referring to FIG. 6, another representative EEG sensor 600 includes electrodes 603-606 situated proximate a perimeter of a circular housing 602. The electrodes 603-606 are coupled to an analog switch 610 that couples selected electrodes to a differential amplifier 612 to serve as signal and reference inputs as instructed by a controller 614. A transmitter 616 is coupled to the controller 614 to communicate measurement results to a remote mobile station or other device or network. The electrodes 603-606 are shown as having circular cross-sections and can be cylindrical electrodes, but other shapes are possible. Typically, distal electrode surfaces includes hooks or other mechanical and/or electrical couplings. While the analog switch 610 can be controlled to designate electrodes as signal and reference electrodes, the analog switch 610 can also sequentially step through some or all combinations and in some cases, discontinue stepping after an electrode arrangement that produces a superior signal level or a superior signal-to-noise ratio is identified.

Referring to FIG. 7, yet another representative EEG sensor 700 includes electrodes 703-706 situated proximate corners of a rectangular housing 702. In typical examples, the electrodes 703-706 are disposable. The electrodes 703-706 are coupled to an analog switch 710 that couples selected electrodes to a differential amplifier 712 to serve as signal and reference inputs as instructed by an MCU 714. The electrodes 703-706 can be corner sections situated within the housing 702. As noted above, distal electrode surfaces generally include hooks or other mechanical and/or electrical couplings. The electrodes 703-706 can alternatively be formed along sides of the housing 702, and need not be corner sections or situated at corners.

Figure 8:
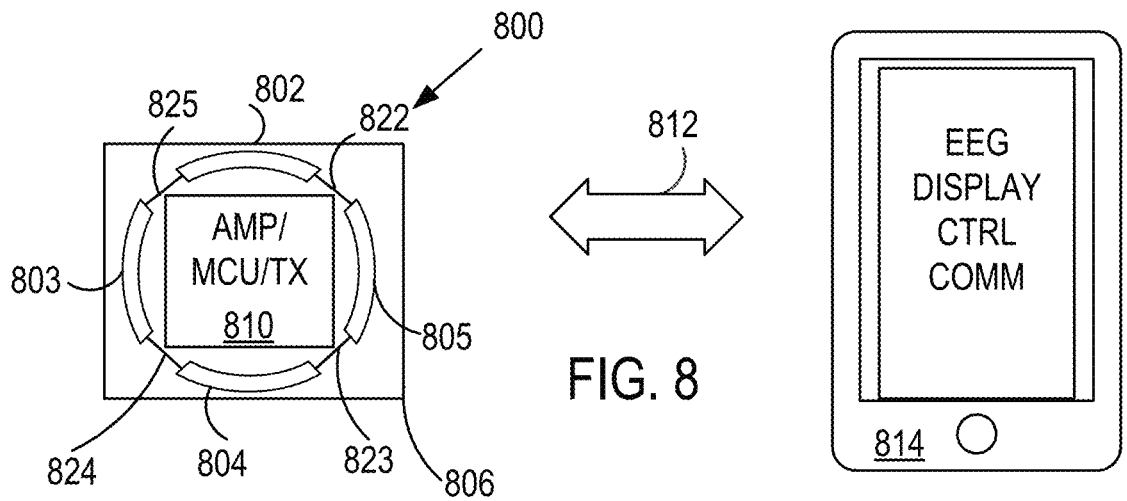
FIG. 8 illustrates wireless communication of EEG data from an EEG sensor to a mobile computing device.

Referring to FIG. 8, an EEG sensor 800 includes electrodes 802-805 (typically disposable) that are secured to a housing or substrate 806. In the example of FIG. 8 and other examples disclosed herein, all the electrodes of an EEG sensor need not be the same, nor must they be similarly or symmetrically situated with respect each other or to an EEG housing. In general, so along as at least two (and preferably) three electrodes are provided, any geometric arrangement of electrodes whether or not of the same shape is sufficient. As noted above, distal surfaces of electrodes can include teeth or hooks, and in the example of FIG. 8 such teeth or hooks can face in common direction and can be differently oriented with respect so that a sliding motion in a predetermined direction can secure the sensor 800 to a surface. Typically, such teeth or hooks are arranged so that a slight rotation such as a clockwise rotation secures the electrodes.

The EEG sensor 800 also includes an electronic assembly 810 such as a circuit board to which amplifier, processor, A/D, transmitter, battery, and other circuit elements can be secured. In the example of FIG. 8, a wireless connection 812 couples the EEG sensor 800 to a mobile computing device 814 or other computing device. In other example, an optical fiber or electrical cables can be used to provide a cabled optical connection. If a cable connection is used, sensor power can be provided by the mobile computing device 814 and the connection can be based on, for example, a Universal Serial Bus.

As shown in FIG. 8, insulating spacers 822-825 can be used to fix the electrodes 802-805 to each other, and if desired, the electronic assembly 810 can be secured to the electrodes 802-805 and a separate support or substrate is unnecessary. If a housing is provided, the electrodes 802-805 generally extend out of the housing at least partially to aid in skin contact.

Figure 9:
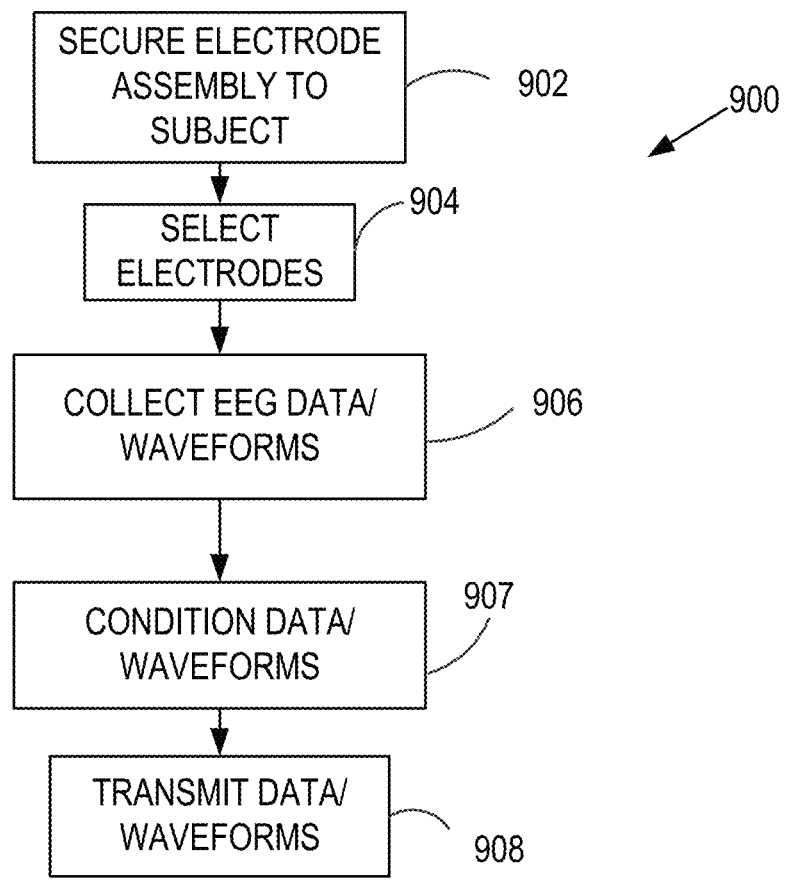
FIG. 9 illustrates a representative method of acquiring EEG data using a remote, subject-mounted EEG sensor.

Referring to FIG. 9, a representative method 900 includes securing an electrode assembly such as a disposable electrode assembly to a subject at 902, typically using hooks, pin, or barbs on one or more EEG electrodes. At 904, electrodes are selected as signal and reference electrodes, or multiple or all combinations are selected for evaluation. In some cases, some or all combinations are evaluated and a combination associated with a preferred signal characteristic such a signal to noise ratio or signal strength is selected. A remote transmitter such as a mobile computing device can be used to communicate a selection of electrodes or all (or predetermined electrode sets) can be used and associated EEG data transmitted with a suitable header that identifies the electrode selection. The electrodes can be selected with, for examples, mechanical or electrical switches, including analog switches. The mobile computing device can then be used to display EEG data, so that a user can enter a command so that a preferred selection is transmitted to the EEG sensor. If EEG waveform power (such as power in a one or more spectral bands) is used, an electrode selection can be made with a power measurement in the EEG sensor or at an external computing device. At 906, EEG waveforms are collected and the collected EEG waveforms are conditioned by filtering or other processes at 907. At 908, data waveforms or other data associated with the selected electrode combinations is transmitted.

Figure 10:
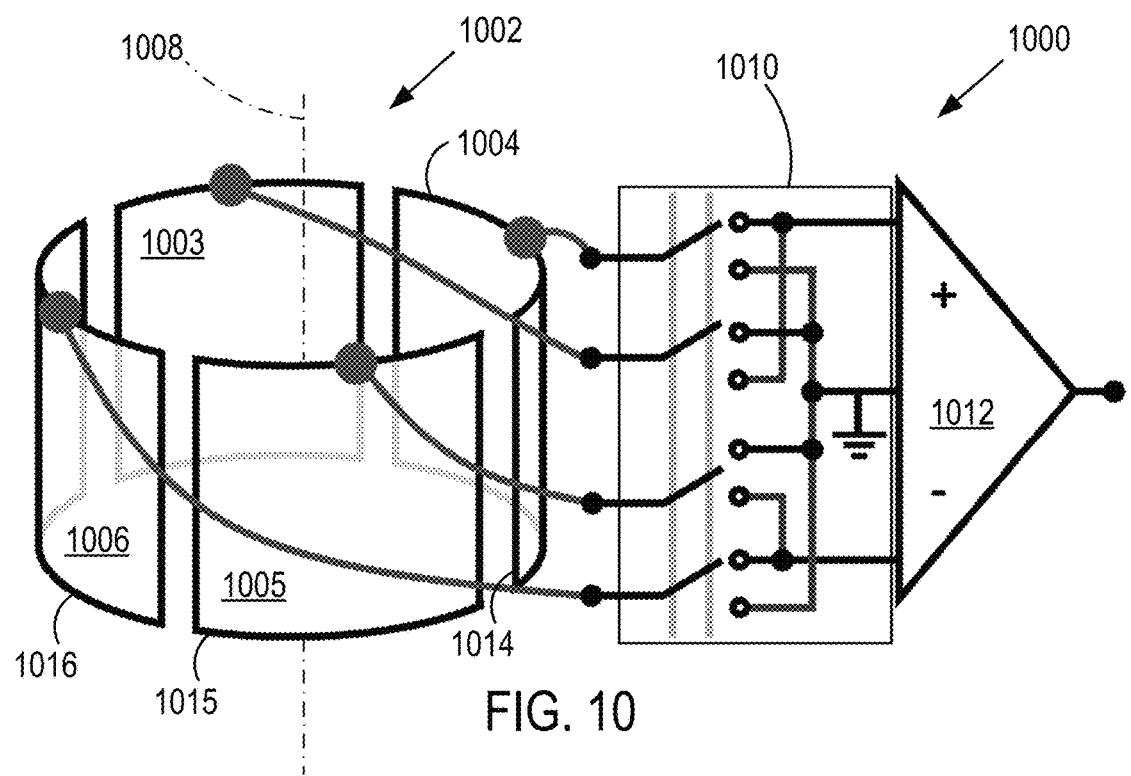
FIG. 10 illustrates an EEG sensor that includes four electrodes that define a hollow cylinder in which ancillary electronics can be situated.

Referring to FIG. 10, a sensor 1000 includes an electrode assembly 1002 in which electrodes 1003-1006 define a hollow cylinder. This hollow cylinder is vertically (i.e., along an axis 1008) decomposed into four electrically isolated, approximately quarter-circle conductive segments corresponding to the electrodes 1003-1006. The electrodes 1003-1006 are coupled to a switch 1010 so that two opposite electrodes (such as 1003, 1005) are connected to differential inputs of an amplifier 1012, and the other two opposite electrodes (such as 1004, 1006) are connected to ground and serve as reference electrodes. The switch 1010 can select pairs of electrodes to serve as signal or reference electrodes either automatically or manually so that the differential input follows a maximum gradient of skin bio-potential for superior signal-to-noise ratio. In some examples, the electrode assembly 1002 is 1.0 cm or 4 mm high along the axis 1008 and has a diameter of about 1.9 cm. Typical diameters can be in the same range as U.S currency such as nickels, dimes, quarters, or pennies, but other diameters can be used. Electronics such as the switch 1010 and the amplifier 1012 can be situated in the hollow cylindrical volume.

Figure 11A:
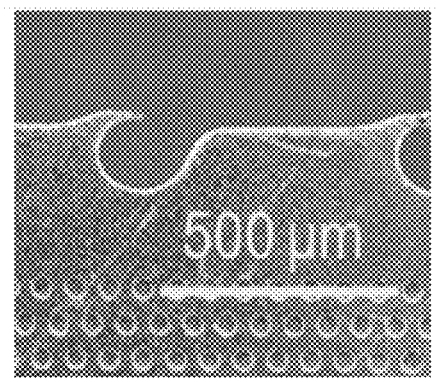
FIGS. 11A-11C are electron micrographs showing electrode teeth (FIG. 11A), a single tooth (FIG. 11B), and nanowires on a tooth (FIG. 11C). These stainless steel microscopic teeth are fabricated using photolithographic techniques as described in Jia et al., U.S. Patent Application Publication US2015/0126846, which is incorporated herein by reference.
Figure 11B:
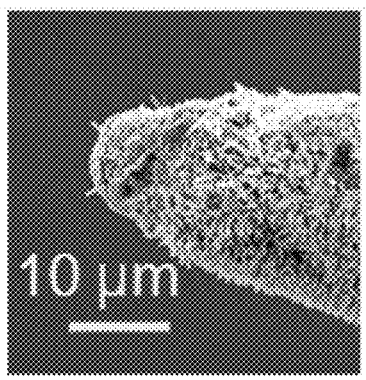
Figure 11C:
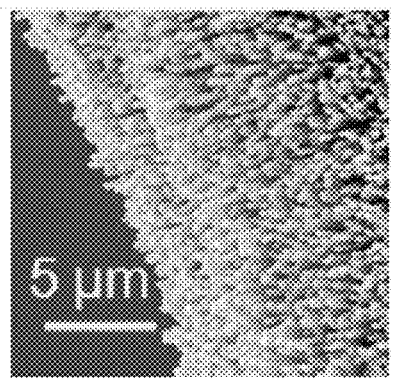

As shown in FIG. 10, distal regions of the electrodes 1003-1006 such as distal regions 1014-1016 are provide with fine teeth or hooks for connection to a top layer of skin (stratum corneum). The details of such distal regions are shown in FIGS. 11A-11C. FIG. 11A depicts fine teeth and FIGS. 11B-11C show nanowires covering the teeth. In some examples, the nanowires are formed of zinc oxide or gold. The teeth are designed to secure the sensor on the skin and electrically connect to the skin. The teeth are generally made of stainless steel, and gold coated to reduce an impedance of the skin-electrode-interface. As used herein, a tooth depth is a tooth dimension associated with a maximum tooth extension from an untoothed portion of a surface, and tooth depths of less than 1 mm, 0.5 mm, and 0.25 mm are preferred.

In one example, a Texas Instruments ADS1294 multi-channel, simultaneous sampling, 24-bit, delta-sigma ($\Delta\Sigma$) analog-to-digital converter with built-in programmable gain amplifiers (PGAs) was used for data acquisition, a 16 bit microcontroller (Texas Instruments MSP430) was used to control data processing and transmission, and an RN-42 Bluetooth module from Roving Networks was used to transmit data. Other component selections can be made, and components that are power efficient and compact are preferred. In some examples, other suitable signal amplifiers, microprocessors, and WiFi adapters (for example, IEEE 802.11ac, 802.11a, 802.11b, or 802.11g adapters) can be used to acquire data, control data processing, and transmit data.

Figure 15:
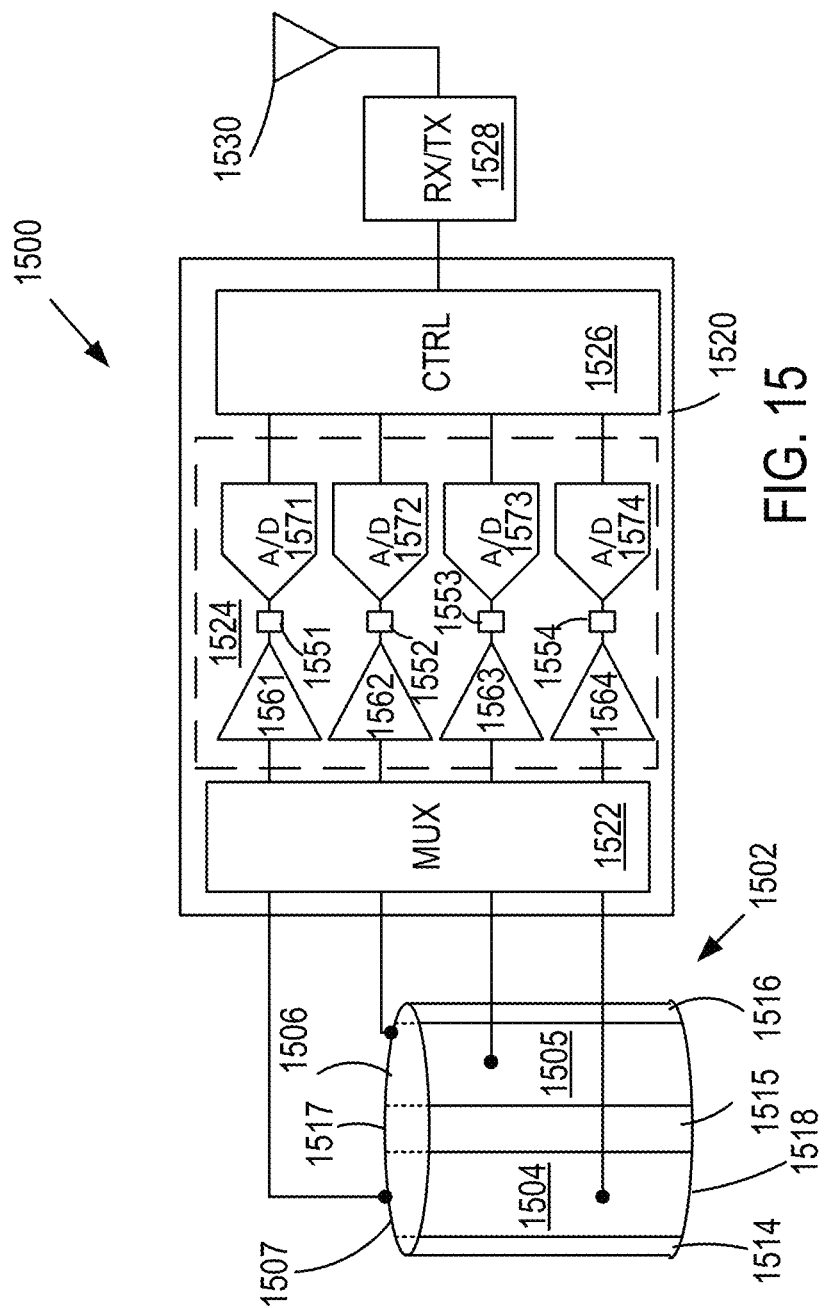
FIG. 15 illustrates an EEG sensor that includes a multi-channel amplifier, a set of filters, and an A/D circuit.

Referring to FIG. 15, an EEG sensor 1500 includes a cylindrical electrode assembly 1502 (that may be disposable) and that includes electrodes 1504-1507 that are separated by non-conductive gaps 1514-1517. A distal surface 1518 of the electrode assembly 1502 is provided with teeth or other skin connections as discussed above. The electrodes 1504-1507 are electrically connected to a multichannel amplifier and A/D circuit 1520 that includes a set 1524 of amplifiers 1561-1564, A/Ds 1571-1574, and filters 1551-1554, and a multiplexer 1522 that selects electrode couplings to the amplifiers and A/Ds. Digitized outputs are coupled to an onboard controller 1526 and coupled to a transmitter 1528 and antenna 1530. Outputs associated with some or all combination of electrodes as references and signals can be transmitted as desired. Circuitry, including a battery, can be situated within the electrode cylinder. If more convenient, a single electrical cable can be used to communicate data. For example, a twisted pair or a multi-conductor cable such as an Ethernet cable can be used, and EEG data communicated in series or in parallel.

Demonstration Example

Figure 12:
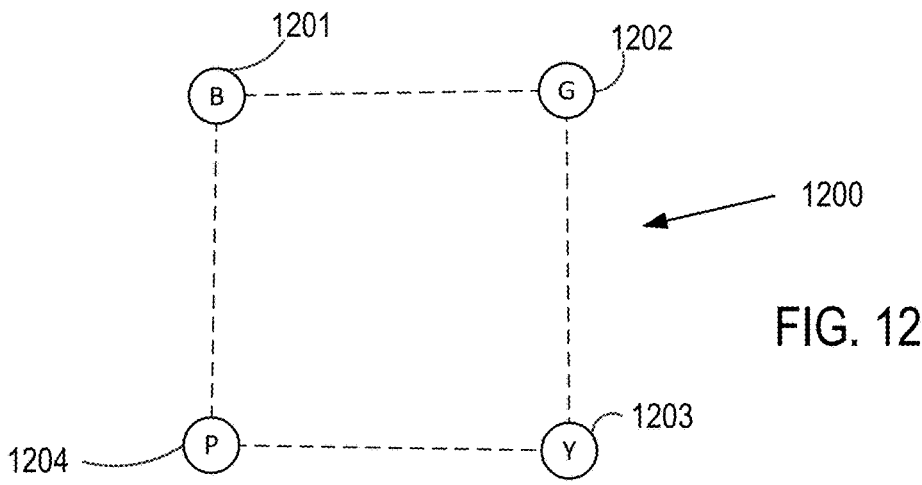
FIG. 12 illustrates disk electrode separation used to validate the utility of closely spaced EEG electrodes.

The EEG sensors disclosed herein are generally particularly advantageous if the EEG sensors are both small and readily attachable to a subject. While electrodes can be secured to an EEG sensor so as to extend beyond a sensor housing, more robust EEG sensors typically have electrodes within or mounted directly to a sensor housing or other sensor substrate. In such compact EEG sensors, electrode separation tends to be smaller than that which is generally believed necessary for successful EEG measurements. To demonstrate the utility of small separations, the electrode arrangement 1200 of FIG. 12 was used. The electrodes 1201-1204 were conventional disc electrodes that were placed in an occipital region of a male, healthy subject's scalp.

Separations of about 20 mm were selected for evaluation. The EEG signal is generated by functional neural substrates within the brain and the EEG signal at the scalp surface can be associated with volume conduction in response to current sources at activated neural substrates. Two of four electrodes 1201-1204 were connected to a differential amplifier as signal inputs, and the remaining two electrodes were connected together and further connected to a reference input of the same amplifier. Since any two of the electrodes could be used as signal inputs, there were six ways of connecting these electrodes corresponding to different orientations. It is possible that some of the six ways provide better signal qualities than others.

Inter-distances of the electrodes were 20, 22, 22 and 25 mm for electrodes pairs BG, BG, PY, GY, respectively. EEG data were acquired using an instrumentation amplifier, gain amplifiers and sets of high-pass and low-pass filters. Data was recorded at a sampling rate of 500 Hz with 16-bit resolution, and recorded data displayed in real-time, as needed.

In order to verify that a true EEG signal has been recorded, signal and noise in the acquired raw data must be identified. Unfortunately, signal and noise are practically impossible to entirely separate. Therefore, the alpha wave as a signature signal is identified from recorded signal to determine the signal quality. Alpha waves are associated with alertness and wakefulness and exhibit a definite rhythm when a subject is relaxed with eyes closed, and almost disappear for an alert subject with open eyes and alpha wave frequencies are generally in the range of 8-13 Hz. These known characteristics of alpha waves allowed their use in assessing different electrode orientations.

Raw EEG data was divided into 5 segments of duration of 5 seconds (2,500 data points) and a Hamming window with 5-second length was applied to each segment. Each segment was processed by taking a discrete Fourier transform (DFT) of the segment padded with zeros so that DFT length was 4,096. Alpha band energy was defined as the magnitude squared of DFT within an 8 Hz to 13 Hz window. For each electrode orientation/selection, data were acquired and processed in this manner.

Figure 13A:
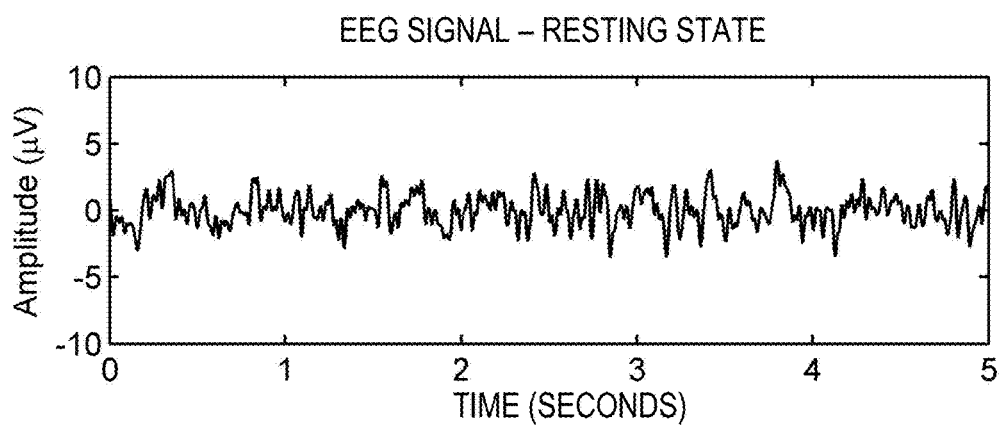
FIGS. 13A-13B illustrate representative EEG waveforms acquired with a subject in a resting state (FIG. 13A) and with eyes closed (FIG. 13B).
Figure 13B:
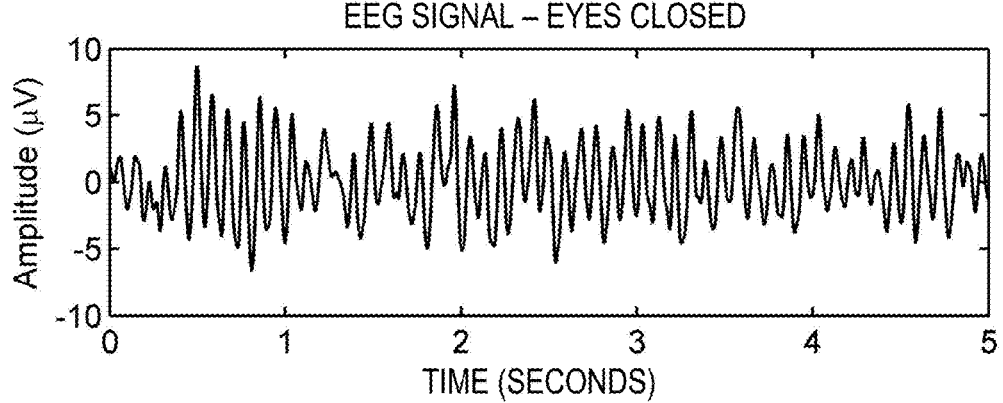

To confirm that alpha wave acquisition was appropriate, waveforms were acquired with the YB electrode pair use as a reference. The resulting resting state (eyes open) and eyes closed state waveforms are shown in FIGS. 13A-13B, confirming that the alpha wave was observable. Different electrode combinations were then investigated with the subject's eyes closed and signal power measured as summarized in the table below.

| Alpha wave power and peak frequency for various electrode combinations | | | | | | |
|---|---|---|---|---|---|---|
| Reference Connection | YB (1) | GP (2) | GY (3) | BG (4) | BP (5) | PY (6) |
| $f_{Peak}$ (Hz) | 11.72 | 11.84 | 11.72 | 11.25 | 11.72 | 11.72 |
| Power (dB) | −23.35 | −22.9 | −23.76 | −29.86 | −25.47 | −29.14 |

Figure 14:
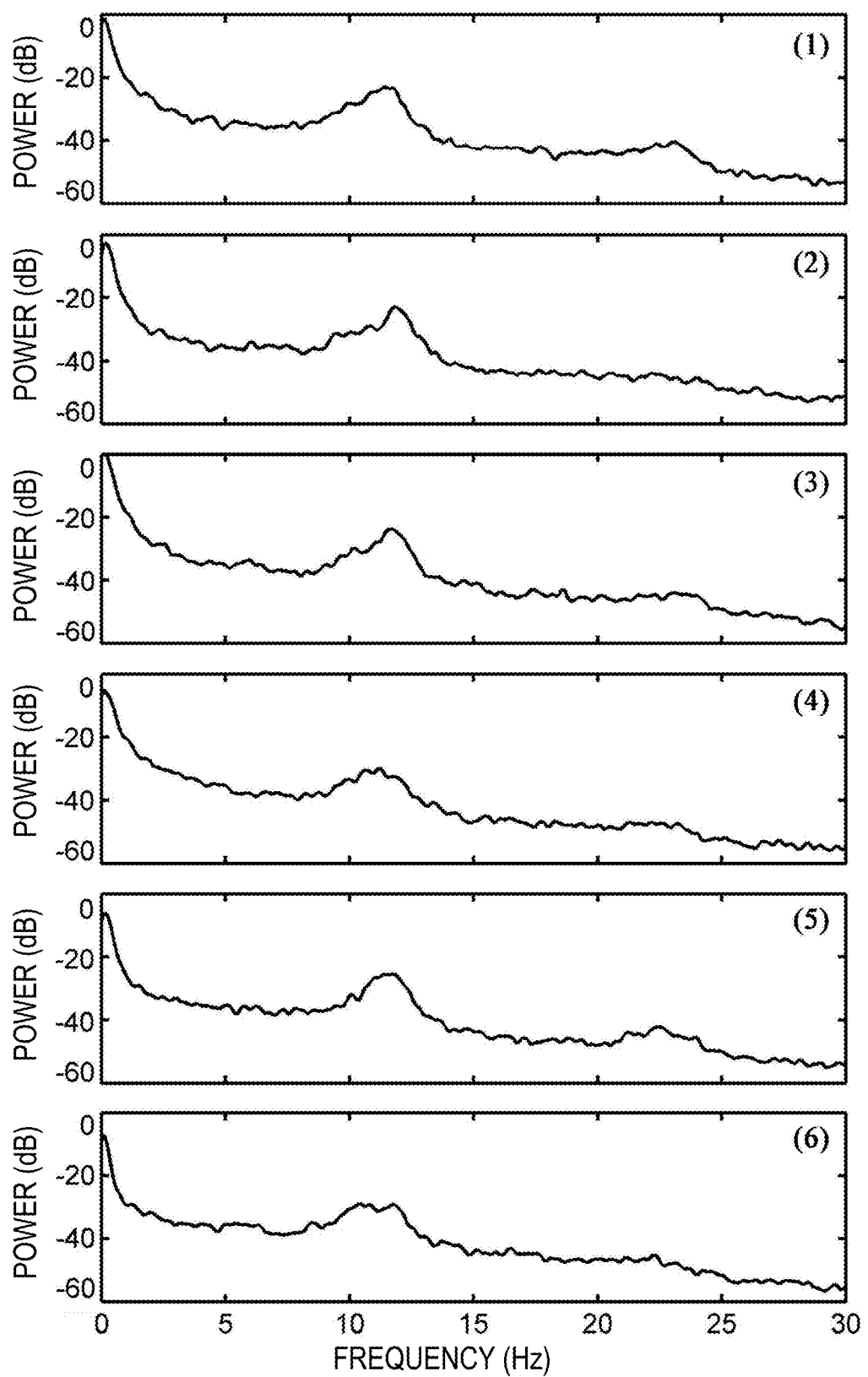
FIG. 14 contains spectral plots of alpha wave power for various electrode orientations.

FIG. 14 contains graphs of averaged spectral power for all six electrode arrangements, all of which exhibit alpha waves. As can be observed from the table above, EEG waveforms can be acquired with closely spaced electrodes, and selections of different signal and reference electronics provide different signal powers.

Additional Examples

Figure 16A:
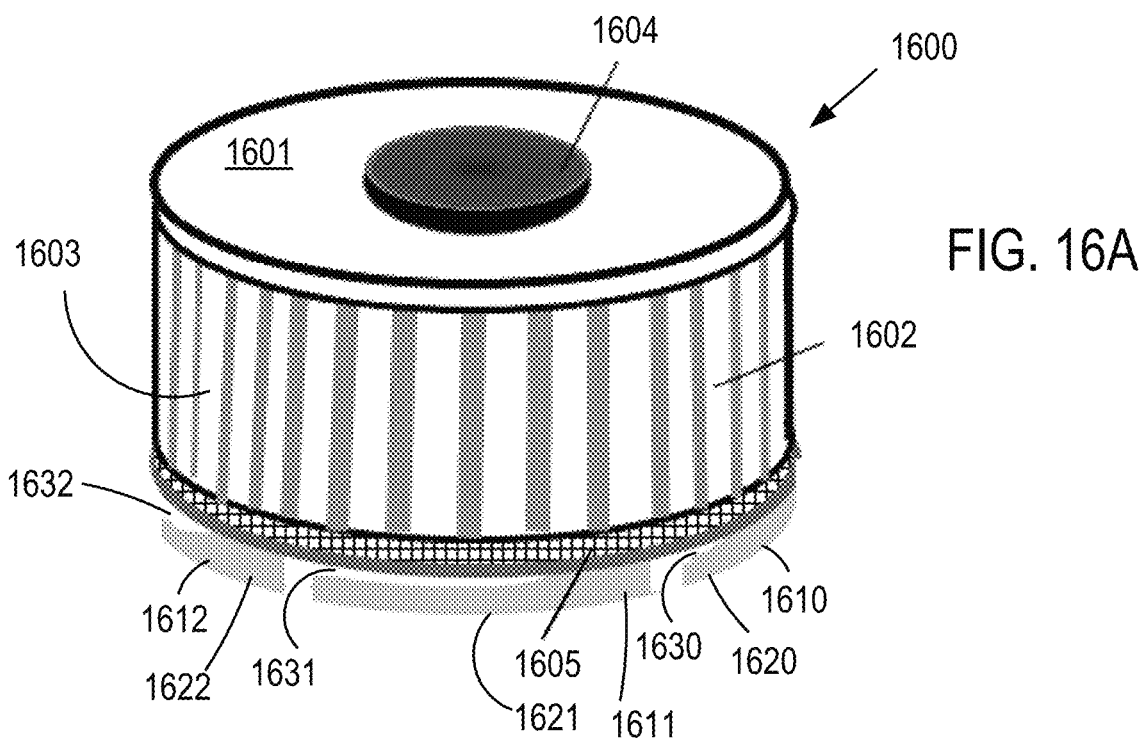
FIGS. 16A-16C illustrate an EEG sensor that includes a disposable disk to which electrodes are secured.
Figure 16B:
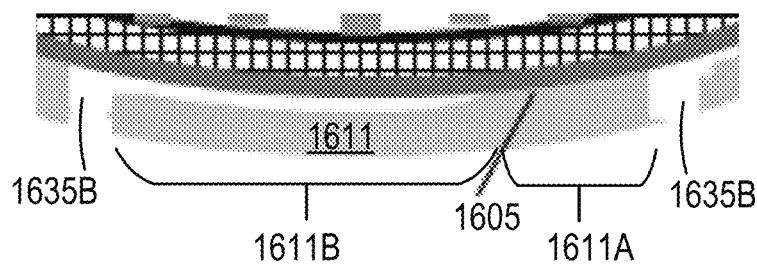
Figure 16C:
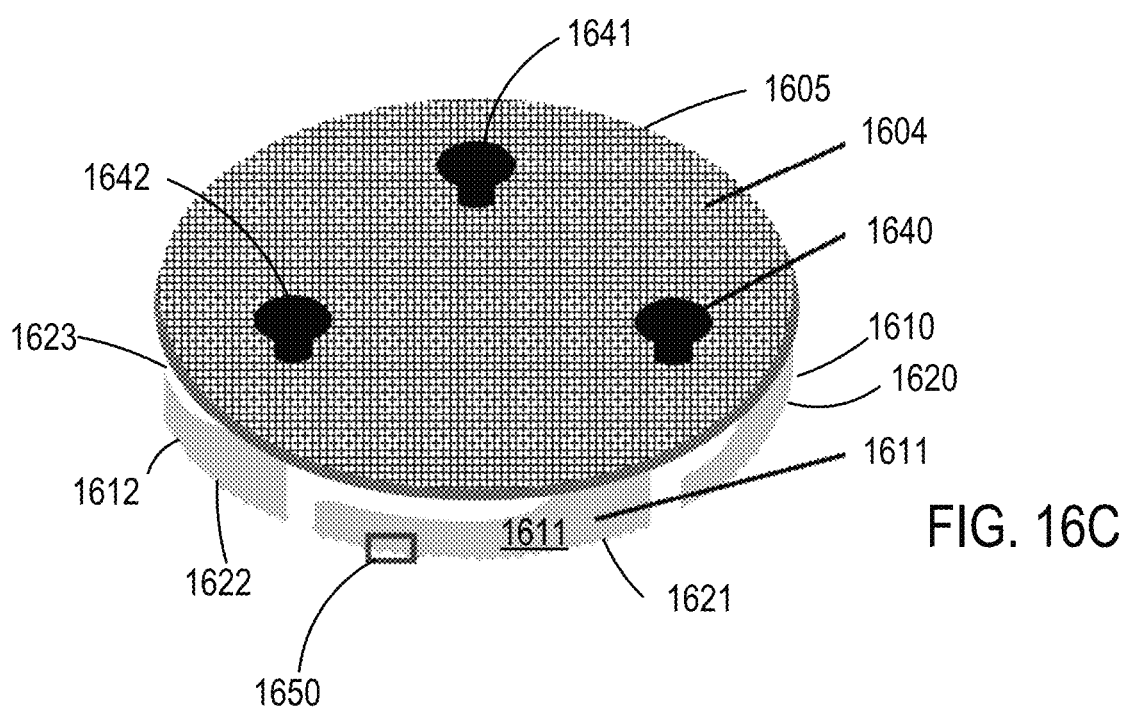

Referring to FIGS. 16A-16C, a sensor 1600 includes a housing 1602, shown as a cylindrical housing, that defines a volume in which circuit components such as A/D convertors, amplifiers, buffer circuits, microcontrollers, RF transmitters (or transceivers, analog switches, batteries, circuit boards, and other components can be situated. A power switch 1604 (such as push-button switch) is provided on an end surface 1601 of the housing 1602 at an upper end and can include an indicator light such as an LED to aid the user in determining that the sensor 1600 is active. A perimeter surface 1603 can be knurled or otherwise provided with elements, preferably surface features that extent along a central axis of the housing 1602. Other grip aids or grip promoting materials can be used instead on in addition to knurling. The housing 1602 is preferably liquid proof to permit sterilization. A disposable disk substrate 1605 (typically a plastic disk) is situated at a distal end of the housing 1602 and attachment electrodes such as representative attachment electrodes 1610-1612 that include representative toothed distal surfaces 1620-1622 are secured to the disk substrate 1605. Each of the attachment electrodes 1610-1612 is shaped in a boot form to allow slight motion in a vertical direction so as to conform to a subject scalp surface. Typically, the electrodes 1610-1612 approximately conform to the cylindrical shape of the perimeter surface 1603, and define respective gaps 1630-1632 that separate electrode end portions form the disk electrode 1605. For example, as shown in FIG. 16B, the electrode 1611 includes an end portion 1611B and a portion 1611A that is secured to the disk substrate 1605, and the gap 1631 is situated between the end portion 1611B and the disk substrate 1605. Other electrodes are similarly constructed and secured. This electrode shape can be referred to as boot-shaped, and permits electrode flexing to conform to a subject surface. Typically four electrodes are provided, but for convenient illustration, only three electrodes are shown in FIGS. 16A-16B. In some examples, the electrodes are formed of 25 μm thick gold-plated stainless steel but other conductors and thicknesses can be used. As noted above, housings need not be cylindrical but can have rectangular, polygonal, ellipsoidal or other cross-sections.

Referring to FIG. 16C, clip posts 1640-1642 are fixed to the disposable disk substrate 1605 to retain a battery such as a coin-shaped battery on either surface of the disk substrate 1605 and to couple electrical power to sensor circuitry. The disk substrate 1605 can be provided with conductors situated to couple each of the electrodes to suitable circuit elements as discussed above, typically one or more analog switches and/or amplifiers. The distal surface 1621 of the electrode 1611 can have surface features such as shown in FIGS. 11A-11C. Typically teeth are formed that are 30-50 μm high at an angle of 2-5 degrees from the plane defined by the disk substrate 1605, and include a plurality of nanowires. In the arrangement of FIGS. 16A-16C, the disk electrodes 1605 can be disposable, and typically the entire disk assembly of FIG. 16C is disposable.

FIG. 17 illustrates a method of manufacture electrodes such as described above. Referring to FIG. 17, at 1702 a photoresist layer is applied to a conductive sheet to sensitize the sheet, and at 1704, the sensitized sheet is exposed to patterned illumination, by for example, projecting a pattern onto the sensitized surface or by contact printing. In still other examples, patterned photoresist can be provide by direct writing using, for example, an ink jet printing process. At 1706, portions of the photoresist layer is removed, either the exposed or the unexposed portions. At 1707, the conductive sheet is etched to form electrodes. In some examples, multiple electrodes are defined on a single conductive sheet as an electrode strip. At 1708, the electrode strips are separated into individual electrodes. As shown in FIG. 18, a conductive strip 1800 which defines multiple electrode strips 1810-1817 can be separated into two, three, or more electrodes.

Figure 19:
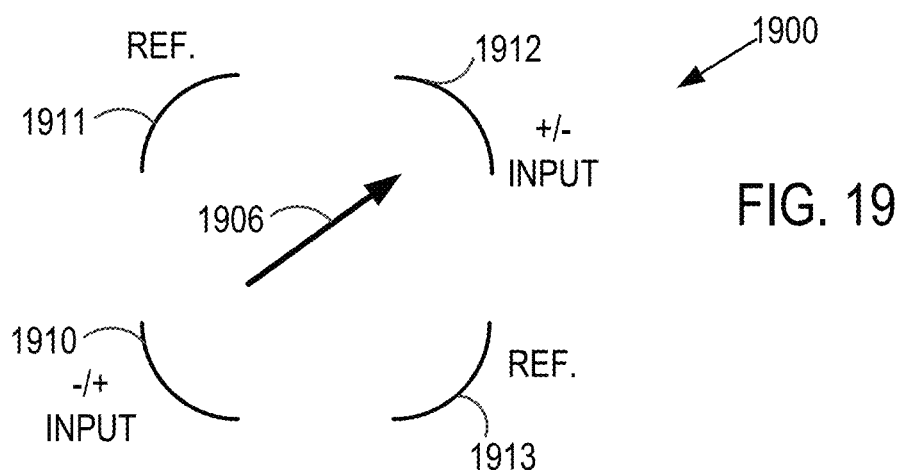
FIG. 19 illustrates electrode selection with respect to a scalp electric field direction.

Inclusion of multiple electrodes can permit selection of preferred electrodes for EEG acquisition. Typically, electrodes that are opposing with respect to a gradient of scalp electrical potential (i.e., scalp electric field) are preferred. This direction is typically variable but changes relatively slowly. FIG. 19 illustrates an arrangement of electrodes 1910-1913 with respect to a scalp electric field direction 1906 to provide superior sensor signal such as signal magnitude and/or signal to noise ratio. In the arrangement of FIG. 19, electrodes 1910, 1912 are coupled to amplifier inputs, and electrodes 1911, 1913 are coupled to serve as a reference. As discussed above, a switch can be provided to vary these couplings and thus select suitable couplings for an arbitrary electric field direction. However, with four electrodes, alignment errors can be significant.

Figure 20:
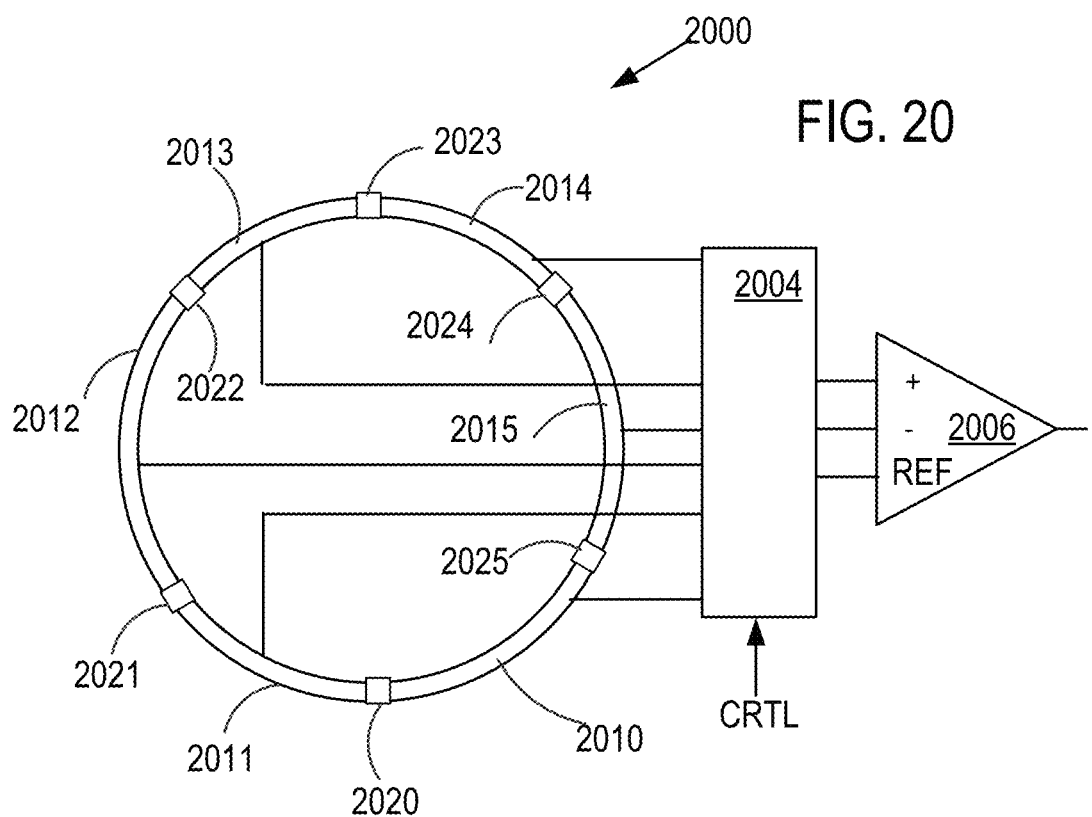
FIG. 20 illustrates an EEG sensor that includes six electrodes.

Superior electrode couplings with respect to an electric field direction can be provided with additional electrodes. With reference to FIG. 20, a sensor 2000 includes electrodes 2010-2015 that are separated by insulating regions 2020-2025. Such electrodes can be formed on an interior or exterior surface of a housing, or as conductors secured to disk substrate as discussed above. The electrodes 2010-2015 need not have the same dimensions and need not be symmetrically situated as shown in FIG. 20. The electrodes 2010-2015 are coupled to a switch 2004 that couples one or more electrodes to differential inputs and a reference input of an amplifier 2006. A control signal is received by the switch to select suitable couplings, typically to produce a preferred signal strength or signal to noise ratio.

Figure 21:
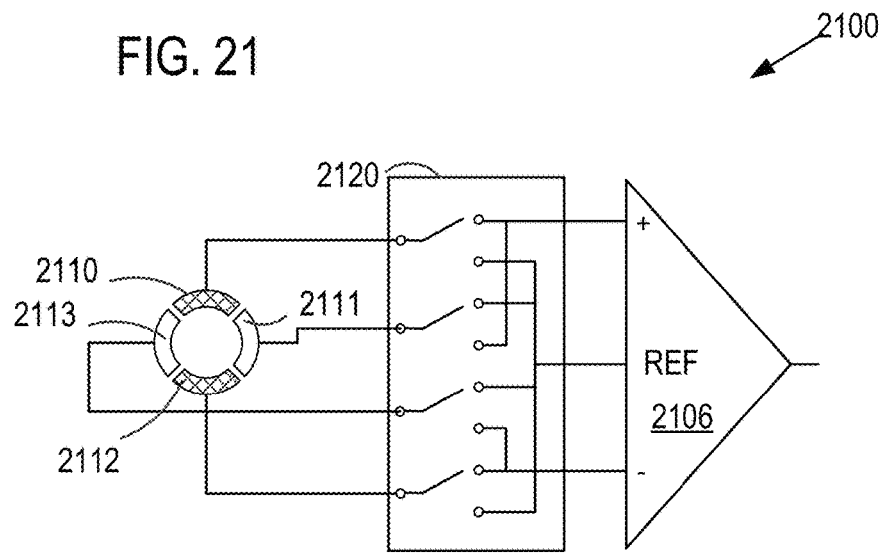
FIG. 21 illustrates electrode switching based on scalp electric field direction.

FIG. 21 illustrates a representative arrangement of electrodes in a sensor 2100. Electrodes 2110-2113 are coupled to a switch 2120 that selectively couples electrodes to differential inputs and a reference input of an amplifier 2106. As shown, electrode 2110 can be switched to connect to a positive input of the amplifier 2016 or the reference (REF) input. The opposite electrode 2112 can be switched to connect to a negative input of the amplifier 2106 or the reference input. Thus, the electrodes 2110, 2112 can be coupled together to serve as a reference, or coupled to opposing amplifier inputs, as preferred based on a scalp electric field direction. Similarly, electrode 2111 can be switched to connect to a positive input of the amplifier 2016 or the reference input. The opposite electrode 2113 can be switched to connect to a negative input of the amplifier 2106 or the reference input. Thus, the electrodes 2111, 2113 can be coupled together to serve as a reference, or coupled to opposing amplifier inputs, as preferred based on a scalp electric field direction.

Figure 22:
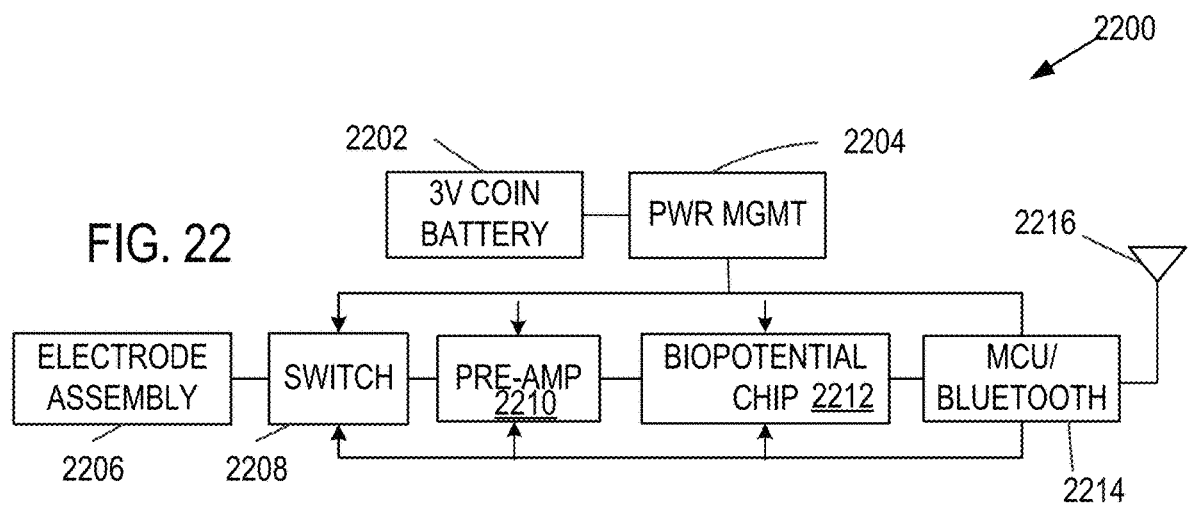
FIG. 22 is a block diagram of a representative subject-mountable, integrated EEG sensor system.

With reference to FIG. 22, a representative sensor 2200 includes a battery 2202 such as a CR2032 battery coupled to one more power management circuits including voltage regulator circuits such as a Texas Instruments TPS 71725 voltage regulator, and a buck-boost convertor such as a TPS63000 buck-boost converter so as to provide sensor power. An electrode assembly 2206 is coupled to an electronic switch 2208 such as an Analog Devices ADG788 quad SPDT switch which is in turn coupled to one or more preamps 2210 such as an INA103 Burr-Brown instrumentation amplifier and a Texas Instruments ADS1292 operational amplifier that can produce a differential signal output. A biopotential circuit 2212 such as a Texas Instruments ADS1292 that includes A/D convertors, a programmable gain amplifier (typically used for EKG and sports and fitness applications) receives the differential signal and couples a digital signal to a microcontroller 2214 such as a Texas Instruments CC2541 microcontroller with a wireless transceiver that implements BLUETOOTH wireless communication via an antenna 2216 that can include a chip antenna such as a Johanson 2450AT42A100 ceramic chip antenna and a balun/filter such as a Johanson 2450BM15A000 impedance matched balun and band pass filter. Sensor electronics illustrated in FIG. 22 can be implemented using one or more circuit substrates sized to fit within a housing, and adjustments to gains, filter frequencies and date flows can be controlled via a remote computing device such as a handheld device.

Example Electrode-Skin Interfaces

Figure 23:
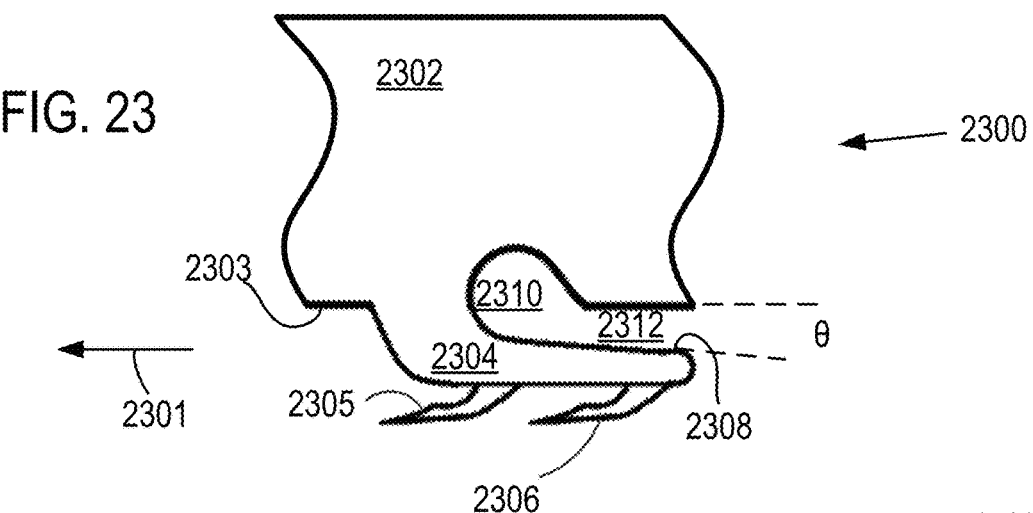
FIGS. 23-26 illustrate portions of representative electrodes suitable for electrical coupling to a skin surface.

With respect to FIG. 23, an electrode 2300 includes an electrode base 2302 having a distal surface 2303 which is provided with representative teeth 2305-2306 situated on an electrode extension 2304. Typically, the distal surface 2303 is a rim of a cylinder and the electrode 2300 conforms to a cylindrical surface. The electrode extension 2304 extends opposite a direction 2301 along which the teeth 2305-2306 face, i.e., opposite a direction in which the teeth 2305-2306 are moved for attachment to a skin surface. An upper edge 2308 of the electrode extension 2304 and the distal surface 2303 define a gap 2312. In addition, the electrode extension 2304 extends from the electrode base 2302 so as to define an aperture 2310. As shown in FIG. 23, the upper edge 2308 of the electrode extension 2304 is situated at an angle θ with respect to the distal surface 2303. The angle θ is shown as a positive angle and is typically within a range of 0 to 0.5 degrees, 0 to 1 degree, 0 to 2 degrees, 0 to 5 degrees, or 0 to 10 degrees, but negative angles can also be used.

As shown in FIG. 23, the electrode 2300 is shown schematically and generally not to scale, but the electrode extension 2304, the gap 2312 and the aperture 2310 are shown to scale. Only two teeth are shown, but more are typically provided. Similarly, only a single electrode extension is depicted, but one or more can be used for each electrode. The gap 2312 and the aperture 2310 provide flexibility so that when pressed against a skin surface, the distal surface 2303 (such as an electrode rim) can conform to a curvature of a scalp surface and distribute forces more evenly. This generally permits more teeth to engage a skin surface and reduces damage to the teeth. This is particularly useful for relatively large electrodes. Fabrication of an electrode such as the electrode 2300 can be done with a photolithography/etching process as discussed above, with little or no additional cost.

Figure 24:
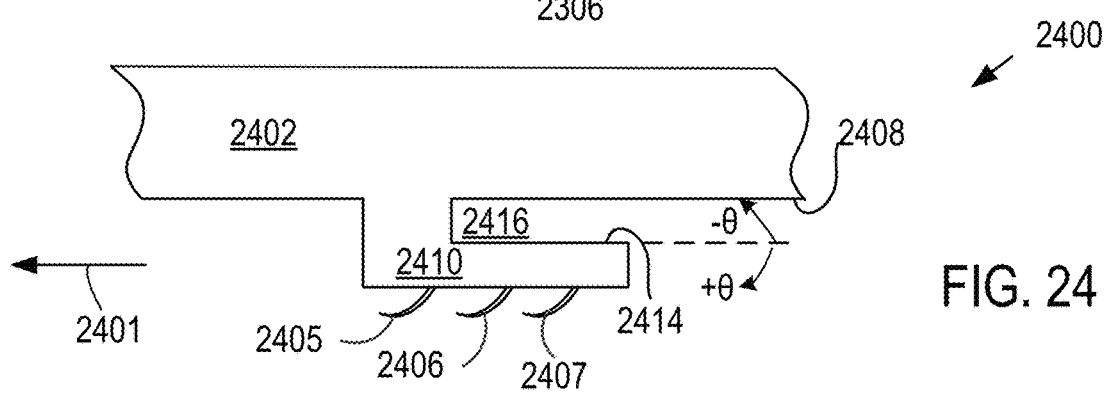

Referring to FIG. 24, a representative electrode 2400 includes an electrode base 2402 that includes an electrode extension 2410 situated at a distal surface 2408. Teeth 2405-2407 extend from the electrode extension 2410 so as to face an attachment direction 2401. An upper edge 2414 of the electrode extension 2410 and the distal surface 2408 define an angle θ that is typically less than 5 degrees. The electrode extension 2410 defines a gap 2416 from the distal surface 2408.

Figure 25:
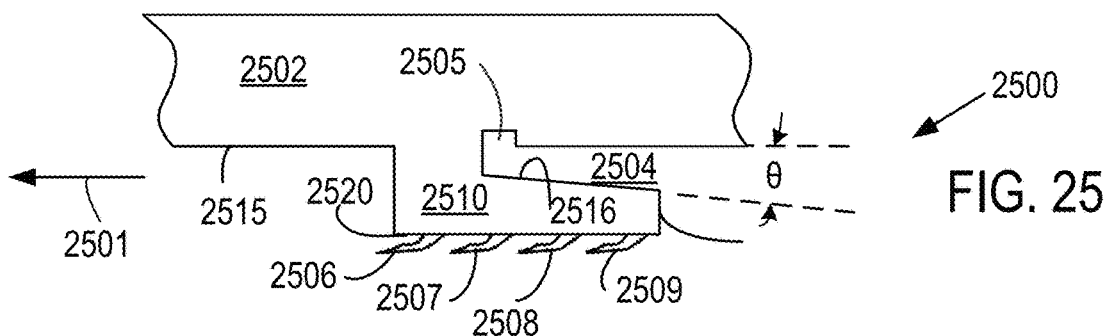

In another example shown in FIG. 25, a representative electrode 2500 includes an electrode extension 2510 that defines a gap 2504 and an aperture 2505 from an electrode base 2502. Teeth 2506-2509 are situated at a distal surface 2520 of the electrode extension 2510 and face an attachment direction 2501. An upper surface 2516 of the electrode extension 2510 and a distal surface 2515 are at an angle θ that is typically less than 1, 2, or 5 degrees.

Figure 26:
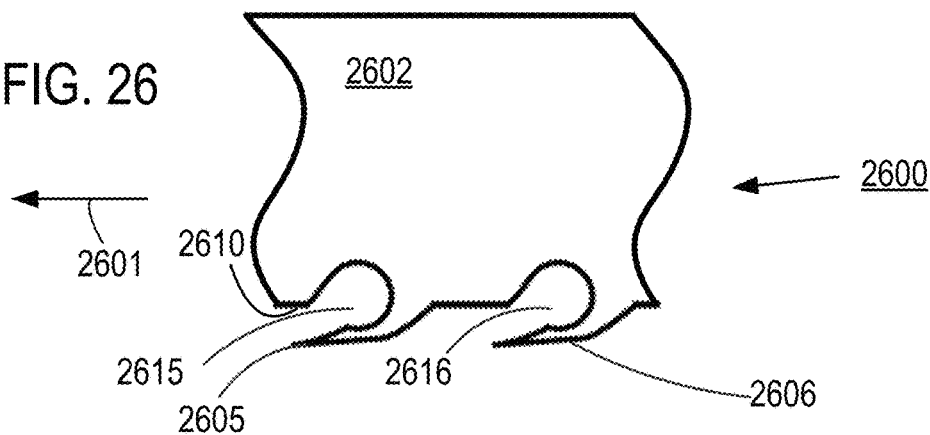

Referring to FIG. 26, a representative electrode 2600 includes an electrode base 2602 that has representative teeth 2605-2606 situated at a distal surface 2610 of the electrode base 2602. The teeth 2605, 2606 face an insertion direction 2601 and define respective relief regions 2615, 2516. While FIG. 26 is generally not to scale and only a portion of the electrode 2600 is illustrated, the teeth 2605-2606 are shown to scale. As with other examples discussed above, the electrode 2600 and the teeth 2605-2606 can be formed in a single piece by a photolithography and etching process, and multiple electrode strips can be formed of a single electrode substrate. As with other electrodes discussed above, it is generally convenient to form the teeth and other electrode portions with a single electrode substrate, but electrodes and teeth can be formed separately and teeth attached to the electrode, but this is generally less suitable than unitary construction.

In view of the many possible embodiments to which the principles of the disclosed technology may be applied, it should be recognized that the illustrated embodiments are only preferred examples of and should not be taken as limiting the scope of the technology. Rather, the scope of the invention is defined by the following claims. We therefore claim all that comes within the scope and spirit of these claims.

We claim:

1. An EEG sensor, comprising:
a housing having a circular perimeter and defining a cavity;
an EEG electrode assembly including at least three boot-shaped EEG electrodes fixed with respect to each other, wherein the at least three boot-shaped EEG electrodes are arcuate electrodes situated at the circular perimeter of the housing;
a differential amplifier situated within the cavity and coupled to the at least three boot-shaped EEG electrodes such that first and second boot-shaped EEG electrodes are coupled to respective differential amplifier inputs and a third boot-shaped EEG electrode is coupled to the differential amplifier as a reference so as to produce an output signal associated with the at least three boot-shaped EEG electrodes; and
a plurality of hooks situated on a distal surface of each of the boot-shaped EEG electrodes and operable to secure at least the three boot-shaped EEG electrodes to a surface of a subject, wherein a proximal surface of each of the boot-shaped electrodes defines a gap so that each of the boot-shaped EEG electrodes is adapted to conform to the surface of the subject.

2. The EEG sensor of claim 1, further comprising:
an analog-to-digital convertor (ADC) coupled to an output of the differential amplifier so as to produce a digital signal corresponding to the differential amplifier output signal; and
a transmitter coupled to the ADC so as to produce a transmitted signal associated with the digital signal corresponding to the differential amplifier output.

3. The EEG sensor of claim 2, wherein the transmitter is a wireless transmitter.

4. The EEG sensor of claim 1, wherein the at least three boot-shaped EEG electrodes are situated on an exterior surface of the sensor housing.

5. The EEG sensor of claim 1, further comprising a switch coupled to the at least three boot-shaped EEG electrodes so as to select the first and second boot-shaped EEG electrodes to be coupled to the differential amplifier inputs and the third boot-shaped EEG electrode to be coupled as the reference.

6. The EEG sensor of claim 1, wherein the at least three boot-shaped EEG electrodes include a fourth boot-shaped EEG electrode, and further comprising an analog switch coupled to the four boot-shaped EEG electrodes so as to select the first and second boot-shaped EEG electrodes to be coupled to the differential amplifier inputs and the third and fourth boot-shaped EEG electrodes to be coupled as the reference.

7. The EEG sensor of claim 3, wherein the wireless transmitter is a radio-frequency transmitter and the electrodes are separated by less than 1 cm.

8. The EEG sensor of claim 1, further comprising:
a substrate secured to the housing, wherein the at least three boot-shaped EEG electrodes are secured to the substrate and the substrate couples the at least three boot-shaped EEG electrodes to the amplifier.

9. The EEG sensor of claim 1, wherein the at least three boot-shaped EEG electrodes are fixed to a disposable disk substrate.

10. The EEG sensor of claim 9, wherein the differential amplifier is fixed to the housing, and the disposable disk substrate is removably secured to the housing.

11. An electrode assembly, comprising:
a cylindrical substrate; and
at least three electrodes secured to the cylindrical substrate, each of the at least three electrodes having a toothed distal surface adapted for attachment to a skin surface, wherein the at least three electrodes are secured to a circular perimeter of a distal surface of the cylindrical substrate and each of the at least three electrodes includes an attachment portion coupled to the cylindrical substrate at the circular perimeter and an extension that extends from the attachment portion and defines a gap from the cylindrical substrate along at least a portion of the extension, and the toothed distal surface is a distal surface of the extension and includes a plurality of teeth.

12. The electrode assembly of claim 11, wherein the cylindrical substrate is a hollow cylindrical substrate.

13. The electrode assembly of claim 11, wherein the cylindrical substrate is a disk, and the at least three electrodes are secured to the disk so that the attachment portions extend from the disk along axes that are perpendicular to the disk.

14. The electrode assembly of claim 11, wherein the plurality of teeth and the extensions face in opposite directions.

15. The electrode assembly of claim 11, wherein each of the plurality of teeth have a plurality of gold-coated nanowires secured to the tooth surface.

16. The electrode assembly of claim 15, wherein the have a tooth depth of less than 0.5 mm and the cylindrical substrate has a diameter of less than 2 cm.

17. A method, comprising:
securing an electrode assembly as recited in claim 11 to electrically connect each of the at least three plurality of electrodes to the skin surface;
processing an electrical signal associated with at least three electrodes for transmission; and
transmitting the processed electrical signal from the electrode assembly.

18. The method of claim 17, wherein the electrode assembly is secured to the skin surface by rotation so that a toothed surface engages the skin surface, and wherein the electrical signal is processed so as to be transmitted as a digital signal.

19. The method of claim 18, wherein the processed electrical signal is transmitted as a radio-frequency signal.

20. The method of claim 17, further comprising selecting, from the at least three electrodes, first and second electrodes associated with the electrical signal to be processed for transmission, and a third electrode as a reference.

21. The method of claim 17, further comprising processing the electrical signal with an amplifier, and selecting, from the at least three electrodes, first and second electrodes to be coupled to amplifier signal inputs and a third electrode to provide a reference.

22. The method of claim 21, wherein the electrode selection is based on a signal magnitude or a signal to noise ratio of the processed electrical signal.

23. An electrode assembly, comprising: an electrode substrate; and at least three electrodes situated at a perimeter of the electrode substrate, each of the at least three electrodes having a distal surface having a toothed surface for attachment to a skin surface, wherein the toothed surface includes a plurality of teeth, each of the plurality of teeth having a plurality of gold-coated nanowires secured to the toothed surface.

* * * * *